United States Patent

Brin et al.

[11] Patent Number: 5,545,149
[45] Date of Patent: Aug. 13, 1996

[54] METHOD OF CATHETER SEGMENT ATTACHMENT

[75] Inventors: David S. Brin, West Newbury; Peter A. Lunn, Beverly; Stuart R. MacDonald, Danvers, all of Mass.

[73] Assignee: Medtronic, Inc., Minneapolis, Minn.

[21] Appl. No.: 236,766

[22] Filed: May 2, 1994

Related U.S. Application Data

[63] Continuation-in-part of Ser. No. 083,840, Jun. 25, 1993, abandoned.

[51] Int. Cl.$^6$ ........................................... A61M 5/32
[52] U.S. Cl. .............................. 604/265; 604/282
[58] Field of Search ........................... 604/200, 202, 604/264, 265; 128/658, 656

[56] References Cited

U.S. PATENT DOCUMENTS

| | | | |
|---|---|---|---|
| 3,890,976 | 6/1975 | Bazell et al. | 604/280 |
| 4,531,943 | 7/1985 | Van Tassel | 604/280 |
| 4,551,292 | 11/1985 | Fletcher et al. | 264/139 |
| 4,563,181 | 1/1986 | Wijayarathna et al. | 604/280 |
| 4,636,346 | 1/1987 | Gold et al. | 264/139 |
| 4,782,834 | 11/1988 | Maguire et al. | 128/344 |
| 4,863,442 | 9/1989 | DeMello et al. | 604/282 |
| 4,886,506 | 12/1989 | Lovgren et al. | 604/280 |
| 4,899,787 | 2/1990 | Ouchi et al. | 604/282 |
| 4,917,667 | 4/1990 | Jackson | 604/96 |
| 5,078,702 | 1/1992 | Pomeranz | 604/280 |
| 5,160,559 | 11/1992 | Scovil et al. | 604/280 |
| 5,221,270 | 6/1993 | Parker | 604/282 |
| 5,222,949 | 6/1993 | Kaldany | 604/282 |
| 5,234,416 | 8/1993 | Macaulay et al. | 604/282 |
| 5,254,107 | 10/1993 | Soltesz | 604/282 |

OTHER PUBLICATIONS

*Handbook of Common Polymrs*, Roff & Scott, editors, CRC Press 1971, pp. 209, 216, 218, 222, 446, 454–455, 600–601.
*Polymer Science 406*, Penn State University, fall 1988, pp. 12–13, section VIII.
Polyuretous: The Bridge Between Silicone Rubbers and Plastics (chart).
Photograph of 7F SciMed Triguide Sample A with Green Transition.

Primary Examiner—C. Fred Rosenbaum
Assistant Examiner—Chalin Smith
Attorney, Agent, or Firm—Hal Patton; Dianne M. F. Plunkett

[57] ABSTRACT

A therapeutic catheter and used in percutaneous transluminal coronary angioplasty with the catheter comprising a shaft (5) a soft tip assembly. The assembly consists of a transition tube (15), a soft tip tube (20), and plug tube (25). The assembly is surrounded by a shrink wrap means. An infrared source (45) is applied to the interface of the shaft (5) and transition tube (15) with the heat being propagated to the transition tube (15) and the soft tip tube (20). The transition tube (15) is formed of materials having a tensile strength of at least 150% of the materials comprising the soft tip tube (20).

24 Claims, 4 Drawing Sheets

METHOD OF CATHETER SEGMENT ATTACHMENT

This is a continuation-in-part of application Ser. No. 08/083,840 filed on Jun. 25, 1993, now abandoned.

FIELD OF THE INVENTION

The present invention relates to catheters, and more particularly, to a method of soft tip attachment.

BACKGROUND OF THE INVENTION

Catheters are tube-like members inserted into the body for diagnostic or therapeutic reasons. One of the therapeutic procedures applicable to the present invention is known as percutaneous transluminal coronary angioplasty (PTCA). This procedure can be used, for example, to reduce arterial build-up of cholesterol fats or atherosclerotic plaque. Catheters must have sufficient stiffness to be pushed through vessels as well as sufficient rigidity to provide a high degree of torsional control. Stiffness or rigidity in the catheter tip poses the danger of puncturing or otherwise damaging a vessel as it twists through the vascular system. It is therefore desirable for catheters to have a soft or flexible distal tip. Examples of such soft tip catheters are known in the art.

The trend toward catheters with larger inside diameters and softer distal tip segments results, however, in a substantially weaker bond between the soft tip and the distal catheter shaft because of the thinner wall thickness and lower tensile strength of the softer materials. The following methods of tip attachment are known in the art.

U.S. Pat. No. 4,531,943 to Van Tassel et al for a "Catheter with Soft Deformable Tip" discloses an embodiment at col. 4, lns. 43–47 wherein the tip member comprises a tubular sleeve which surrounds and fits by means of a lap joint at the distal end of the catheter body and the sleeve extends beyond the distal end thereof by a predetermined length.

U.S Pat. No. 4,551,292 to Fletcher et al for a "Method for Making a Catheter with a Soft, Deformable Tip" discloses a method of tip construction whereby the tip is heated to soften the plastic, then a forming tool is inserted into the catheter lumen distal end and advanced to the point where an annular protuberance of a predetermined outside diameter is forced into the lumen so as to stretch and shape the plastic to conform to the forming tool. The distal end is then cooled and the forming tool removed, leaving a soft, collapsible segment integrally formed at the distal end of the catheter.

U.S Pat. No. 4,563,181 to Wijayarathna et al for "Fused Flexible Tip Catheter" discloses a soft tip formed from a blend of the nylon of the body portion with an ester linked polyether-polyamide co-polymer which is soft and rubbery to render the tip soft to avoid injury to a blood vessel. The tip is fused or welded at a butt joint to the tubular body which is made of a stiffer nylon.

U.S Pat. No. 4,636,346 to Gold et al for a "Preparing Guiding Catheter" discloses an embodiment in col. 5, lines 12–20 wherein the tip portion may be an initially separate member that is affixed to the elongated tubular body by suitable means, such as by heating, by other energy sources, and/or by adhesives or the like. Such assembly can be assisted by the use of a length of shrinkable tubing that is placed over the joint location prior to and during the assembly operation in order to enhance the smoothness and strength of the joint.

U.S. Pat. No. 4,863,442 to DeMello et al for a "Soft Tip Catheter" discloses an embodiment at col. 5, lines 30–52 wherein a sleeve of shrink film is placed over the polyurethane tube and the distal end of the jacket and overlaps the shoulder. With the sleeve of shrink film in place, the distal end of the assembly is heated to a temperature and for a time sufficient to cause the soft polyurethane tube to flow and fill the gap along with any other gaps which may exist between it and the shoulder, outer surface of the core, and the outer surface of the mandrel. The time and temperature is a function of the particular polyurethane used. With one material tested, the temperature was approximately 320 degrees for a duration of approximately five minutes. As the film shrinks under the application of heat, it will somewhat compress the polyurethane and cause it to conform closely to the contours of the mandrel. After the assembly cools, the mandrel may be removed and the shrink film should be stripped from the assembly.

U.S Pat. No. 4,886,506 to Lovgren et al for a "Soft Tip Catheter" discloses a method of achieving a lap joint at col. 2, lns. 60–62 defining a frusto-conical profile on the distal catheter shaft to which the tip is subsequently fused by RF welding, resulting in a lap joint. The tip has a size and shape adapted to be placed over the tapered portion coaxially, and a composition softer than that of the distal end portion that is suitable for bonding to the fustoconically-shaped outer surface.

U.S. Pat. No. 4,899,787, issued to Ouchi et al., discloses a flexible tube having two or more tube sections which are bonded to a tubular core which comprises one or more fabric mesh tubes and one or more metallic tubular spirals. The tube sections are butted together and then fused to the tubular core. A catheter utilizing this tubular core structure possesses undesirable stiffness and rigidity because of the presence of mesh tubes and metallic tubular spirals at the distal end of the catheter shaft. As a result, the tubular core poses the danger of puncturing or otherwise damaging a vessel as the catheter is manipulated through the vascular system.

U.S. Pat. No. 5,078,702 to Pomeranz for a "Soft Tip Catheter" discloses a tip welded to a tubular body. The tip has an inner sheath of a rigid polymeric material encapsulated by an outer sheath of a flexible polymeric material. The inner sheath of both the body and tip portions are formed from the same polymeric material.

U.S. Pat. No. 5,160,559 to Scovil et al for a "Method for Forming a Guide Catheter Tip Bond" discloses setting a mating distal end of a tubular member against a mating proximal end of a soft, deformable tip to form a butt joint. The butt joint is then softened to render the mating proximal and distal ends of the deformable tip and tube flowable. The tubular member and the deformable tip are then oscillated and advanced into one another along a longitudinal axis such that the materials of the mating proximal and distal ends flow into one another creating a connection zone which solidifies to form a lap joint tip bond.

U.S. Pat. No. 5,234,416, issued to Macaulay et al., discloses a distal soft tip comprising at least two relatively short, coaxially disposed flexible tubular elements. The "first tubular element" 17 is secured to the "distal section" 13 of the catheter shaft, and the "second tubular element" 18 which is softer than the "first tubular element" 17 is secured to the "first tubular element" 17. The "first tubular element" 17 incorporates a radiopaque filler to make the distal tip fluoroscopically observable. See col. 5, ln 32–35. The "first tubular element" 17 has a durometer in the range of Shore 80A to 100A while the "second tubular element" 18 has a durometer in the Shore 70A to 90A range. See col. 6, In 54–59. The distal end of the catheter shaft has a circumferential shoulder over which the proximal end of the first tubular element, which is stepped to mate with the shoulder, is placed. The proximal end of the "*second* tubular element" 18 is abutted against the distal end of the "first tubular element" 17. The short tubular elements are joined with the distal end of the catheter shaft by means such as melt fusing or adhesive bonding.

The joints employed to bond the tubular elements of the '416 Macaulay patent suffer from the same problems as the above-referenced prior art. The overlapping joint of the "first tubular element" 17 with the "distal section" 13 of the catheter shaft, similar to the '943 Van Tassel patent, supra, is undesirable because it creates a stress concentration area at the distal end of the catheter shaft in a plane perpendicular to the longitudinal axis of the catheter shaft. The effect of this stress concentration is an unacceptably low bond strength between the catheter shaft and the "first tubular element" 17 when the wall thickness of the catheter shaft is less than 0.3 min. Further, the butt joint design of the "second tubular element" 18 with the "first tubular element" 17, similar to the '181 Wijayarathna patent, supra, does not yield adequate bond strength because of the low surface area of contact and the stress concentration area at the junction of the "first and second tubular elements" 17 and 18 in a plane perpendicular to the longitudinal axis of the catheter shaft. The effect of the low surface area and the stress concentration is inadequate bond strength when the catheter shaft wall thickness is less than 0.3 mm and when soft, typically low tensile strength materials, such as Shore 70A to 90A TECOFLEX® are used for the "second tubular element" 18. The tensile strength ratio of the "first tubular element" 17 TECOFLEX® of EG93A-HT60 compared to the "second tubular element" 18 TECOFLEX® of EG80A is 126% as derived from the manufacturer's specification.

SUMMARY OF THE INVENTION

The present invention addresses the problem created by the trend toward catheters with larger inside diameters and softer distal tip segments. This trend results in a substantially weaker bond between the soft tip and the distal catheter shaft due to thin catheter shaft walls of less than 0.3 mm and to the lower tensile strength of the softer tip materials. Applicants address this problem by employing a transition segment, a heat shrinkable FEP TEFLON® (polytetrafluoroethylene or PTFE) and an infrared radiation source. The transition segment is selected from a group of thermoplastic elastomers having an ultimate tensile strength of at least 45 MPa. The transition segment also has tensile strength of at least 150% of the materials comprising the soft tip tubing.

During assembly, the distal end of the catheter consists of three segments, the transition tubing which is attached to the shaft, the soft tip tubing which is attached to the transition tubing, and the "plug" tubing which is attached to the soft tip tubing for ease of handling during manufacture and into which a support mandrel is inserted. All three segments are surrounded by a tube of heat shrink. The infrared source acts upon the transition tubing with the heat being propagated to the soft tip tubing. After assembly, the plug tubing and part of the soft tip tubing are trimmed off.

The infrared source causes the catheter shaft, the transition tubing, the soft tip tubing and the plug tubing to become flowable while the heat shrink contracts both radially and longitudinally thereby colliding all segments which results in an improved lap joint. With applicant's invention it is not necessary to use prior art methods such as grinding the exterior surface of the catheter body on a centerless grinder to create a zone of lesser thickness proximate to the distal tip of the catheter and form a lap joint by fitting the preformed soft tip member onto the end portion where it is held in place by a suitable adhesive. Such a process is somewhat slow and considering the cross-sectional dimensions of angiographic catheters, slight variations in the wall thickness which occur during the centerless grinding operation can render the resulting catheter unacceptable, decrease the manufacturing yield and increase the manufacturing cost.

DETAILED DESCRIPTION OF THE PREFERRED EMBODIMENTS

Figure 1:
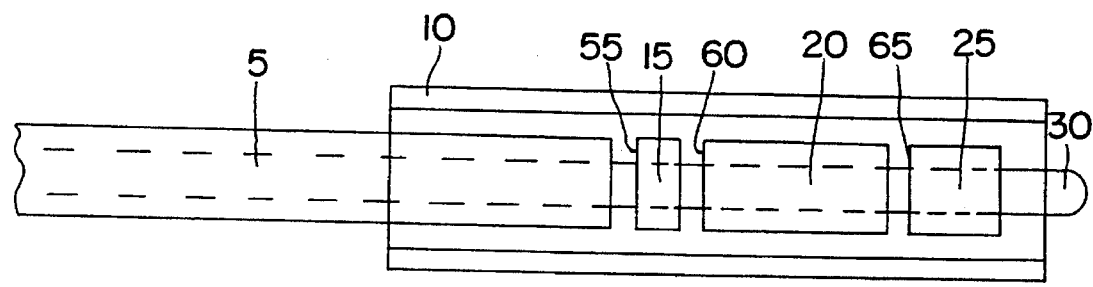
FIG. 1 is the preassembly plan view of the distal end of a guiding catheter constructed according to the invention.

Refer to FIG. 1. To bond a soft tip to the distal end of a guiding catheter shaft 5, insert a TEFLON® coated stainless steel mandrel 30 into the distal end of the shaft 5 with approximately 15.2 cm or 6 inches of mandrel 30 extending beyond shaft 5. Mandrel 30 has an outer diameter approximating the inner diameter of the shaft 5. Advance a segment of 65D Durometer transition tubing 15 over the mandrel 30 and abut the 65D transition tubing 15 to the distal end of the catheter shaft 5. The 65D transition tubing 15 can be made of polyurethane loaded with radiopacifier such as that from Dow chemical company. The 65D transition tubing 15 may have a length of approximately 2.5 mm, a wall thickness of 0.013 inches (0.33 cm) and an inner diameter ranging from a minimum of 0.057 inches (0.14 cm) to a maximum of 0.110 inches (0.28 cm). The catheter shaft 5 can be made of 75D tubing.

Next, advance a segment of 80A Durometer soft tip tubing 20 such as a clear polymer to which titanium dioxide has been added, over the mandrel 30 and abut the proximal end of the 80A soft tip tubing 20 to the distal end of the 65D transition tubing 15. The 80A tip tubing 20 can be made of polyurethane. The 80A tip tubing 20 may have a length of approximately 0.5 cm with a tolerance of plus or minus 1 mm, a wall thickness of 0.013 inches (0.33 cm) and an inner diameter ranging from a minimum of 0.057 inches (0.14 cm) to a maximum of 0.110 inches (0.28 cm). The 0.5 cm length was chosen for handling convenience during the trimming process.

Next, advance a segment of approximately 2.5 mm of 75D plug tubing 25 over the mandrel 30 and abut the proximal end of the 75D plug tubing 25 to the distal end of the 80A soft tip tubing 20. The 75D plug tubing 25 is made of polyurethane and may have a length of approximately 2.5 mm, a wall thickness of 0.013 inches (0.33 cm) and an inner diameter ranging from a minimum of 0.057 inches (0.14 cm) to a maximum of 0.110 inches (0.28 cm).

Finally, slide a segment of approximately 10 cm of TEFLON® polytetrafluoroethylene (PTFE) heat shrink tubing 10 over the mandrel and all tubing segments (65D transition tubing 15, 80A soft tip tubing 20, 75D plug tubing 25) and center the heat shrink tubing 10 longitudinally over the 65D transition tubing 15. Use heat shrink tubing as for example, that from Zeus Industrial.

Figure 6:
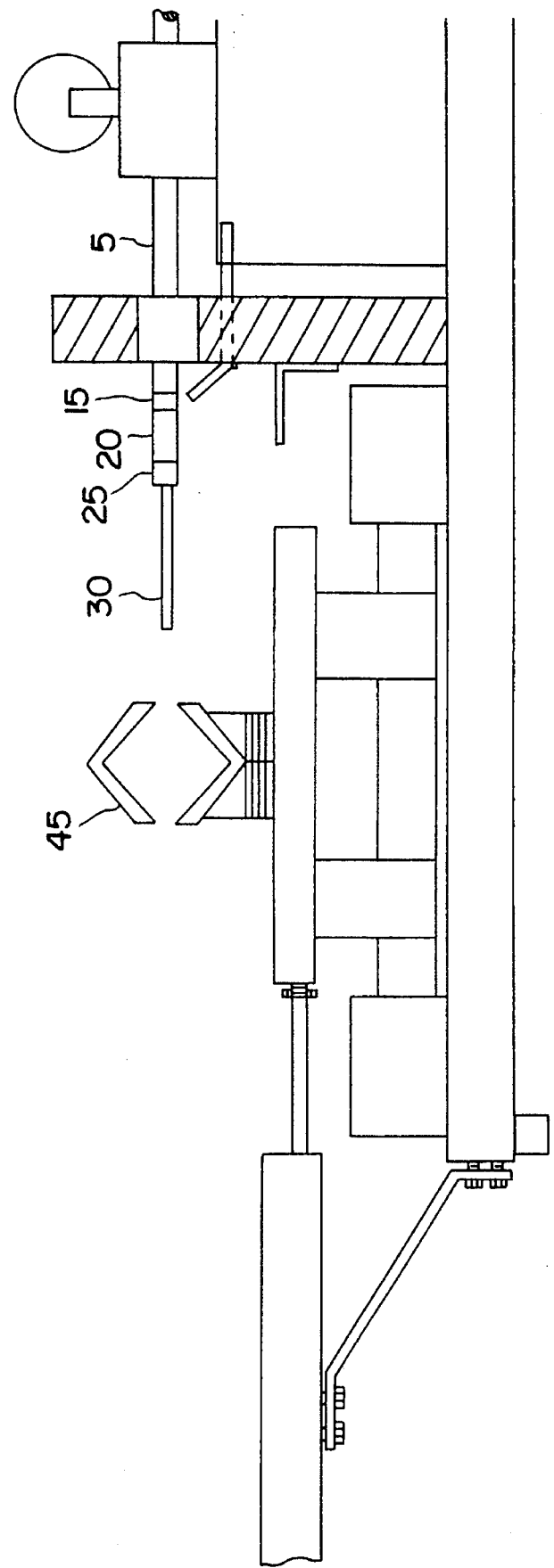
FIG. 6 is the plan view of the infrared assembly.

The manufacturing process has three main phases, heating, cooling and cutting. To begin the heating process, insert the FIG. 2 assembly into a clamping fixture, preferably one with a Programmable Logic Controller (PLC), as for example, that manufactured by General Electric. The PLC will advance the infrared source over the center of the assembly and execute a timed exposure and cooling cycle. An example of such an infrared source 45 is the 25 ohm one-half inch (1.27 cm) Glow-Ring IR radiant heater assembly as for example, that from Eraser, Inc., part number AH 1901 which is depicted in FIG. 6. It includes an aluminum heat sink/socket assembly, Eraser part number IH3H6 and 2 IR elements, Eraser part number IH6515. The following steps will accomplish this. Activate the "start" button on the PLC to begin execution. The infrared source 45 powers up to processing voltage of approximately 50 volts. Insert the FIG. 2 molded tip assembly into the clamping assembly. The operator activates the "cycle on" button and aligns the 65D transition tubing 15 with a marker positioning the infrared source 45 centrally over the 65D transition tubing 15. The PLC clamps the FIG. 2 molded tip assembly and positions the infrared source 45. The PLC timer counts to the heating process value of approximately 30 seconds such that sufficient heat is propagated to allow the shaft 5, transition tube 15, tip tube 20, and plug tube 25 to blend and flow into one another while minimizing concentricity loss. The PLC removes the infrared source 45 from the FIG. 2 molded tip assembly upon the counter reaching the heating process value.

To facilitate bonding the materials, the transition tubing 15 receives greater radiation exposure than the soft tip tubing 20 which compensates for the differences in the two materials' melt characteristics. The infrared radiation elements are chosen to allow sufficient concentration of energy on the interface of the transition tubing 15 and catheter shaft 5 materials, which have higher melt temperatures than the soft tip 20 material. This renders these materials flowable without material degradation from excessive radiation exposure to the soft tip 20 material. The transition tubing 15 material is chosen so that, in catheter wall thicknesses representative of current market trends, sufficient distal soft tip tensile strength is maintained while providing the requisite level of tip softness. Furthermore, the transition tubing 15 must be sufficiently compatible with the catheter shaft material and with the soft tip 20 material so that the materials may be blended together by the application of heat and pressure at the two interfaces while attaining adequate interface bond strengths.

Figure 2:
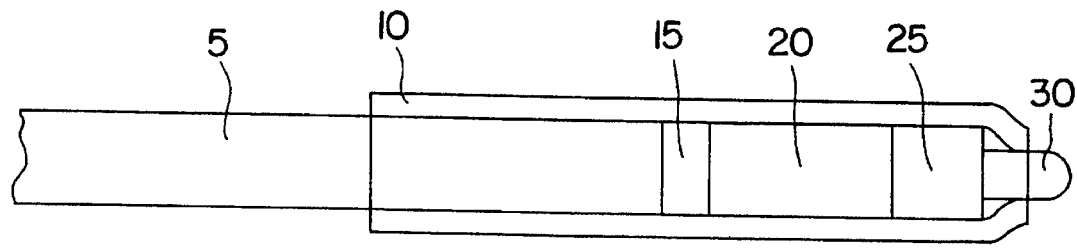
FIG. 2 is the molded tip assembly of FIG. 1.

When the heating cycle is complete, the PLC activates air cooling while counting to a cooling process value of approximately 20 seconds at an ambient air temperature with 80 p.s.i. thereafter deactivating the air cooling and releasing the FIG. 2 molded tip assembly from the clamp fixture. Cooling can be accomplished using a needle valve.

Figure 3:
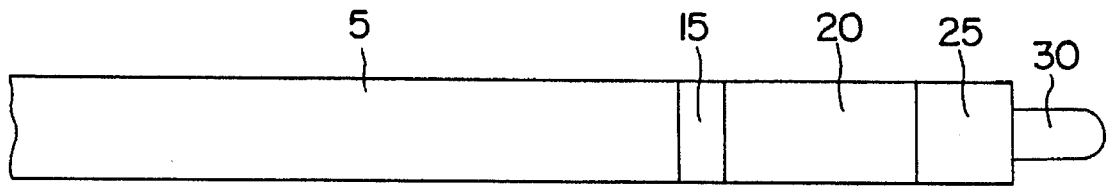
FIG. 3 is the molded tip assembly of FIG. 2 with the heat shrink removed.
Figure 4:
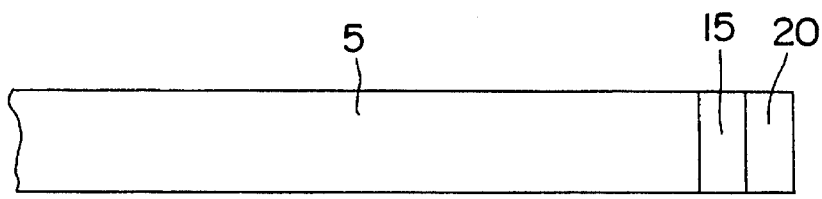
FIG. 4 is the molded tip assembly of FIG. 3 with the mandrel removed and the tip cut to length.
Figure 5:
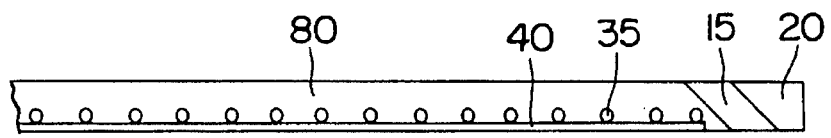
FIG. 5 is the enlarged longitudinal cross section of the distal end portion of the catheter.

The cutting process consists of the operator removing the FIG. 2 molded tip assembly from a clamp fixture such as Carr Lane's part number CFO-01188A and CL-H00-PTC, removing the heat shrink tubing 10 with a razor blade as in FIG. 3, and cutting the FIG. 2 molded tip assembly to length as in FIG. 4. The distal end is trimmed back to a point within the 80A soft tip tubing in a cutting block, resulting in a tip length of 2.5 mm distal to the 2.5 mm 65D transition tubing 15. The TEFLON® (polytetrafluoroethylene or PTFE) coated mandrel 30 is removed from the inside of the now bonded assembly as in FIG. 4. FIG. 5 shows the enlarged longitudinal cross section of the distal end portion of the catheter. The wire braiding 35 in the shaft may stop before, or abut the transition tube 15.

The infrared source 45 is placed over the interface of the 65D transition tubing 15 and catheter shaft 5. Because the interface of the 65D transition tubing 15 and 80A soft tip tubing 20 is off-center from the infrared source, it receives less direct radiation than the interface of the 65D transition tubing 15 and catheter shaft 5. Thus the infrared source 45 acts upon the 65D transition tubing 15 and catheter shaft 5 interface where greater radiation absorption is required to render these materials flowable. Materials thin enough to be used as the 80A soft tip tubing 20 would degrade from excessive radiation exposure if the infrared source were applied directly. The plug tubing 25 must have a higher melt temperature than the 80A soft tip tubing 20 so that it will continuously surround the mandrel 30 without melting under the heat propagation. Once this function is served, the 75D plug tubing 25 will be removed.

The resulting heat shrink tubing 10 contraction, when coupled with heating the tip materials which causes them to expand, results in a local high pressure zone in the tip materials, causing them to blend and flow into one another. A lap joint between the materials is produced. Using 65D transition tubing 15, which is stronger than the 80A soft tip tubing 20, allows thinner walls to be bonded with the shaft, which because of the presence of wire braid 35 and TEFLON® (polytetrafluoroethylene or PTFE) for reinforcement, has a thinner polymer wall thickness. The 65D transition tubing 15, having a larger wall than the catheter shaft 5, because it contains no wire or TEFLON®, offers an improved bond surface for the 80A soft tip tubing 20.

Figure 7:
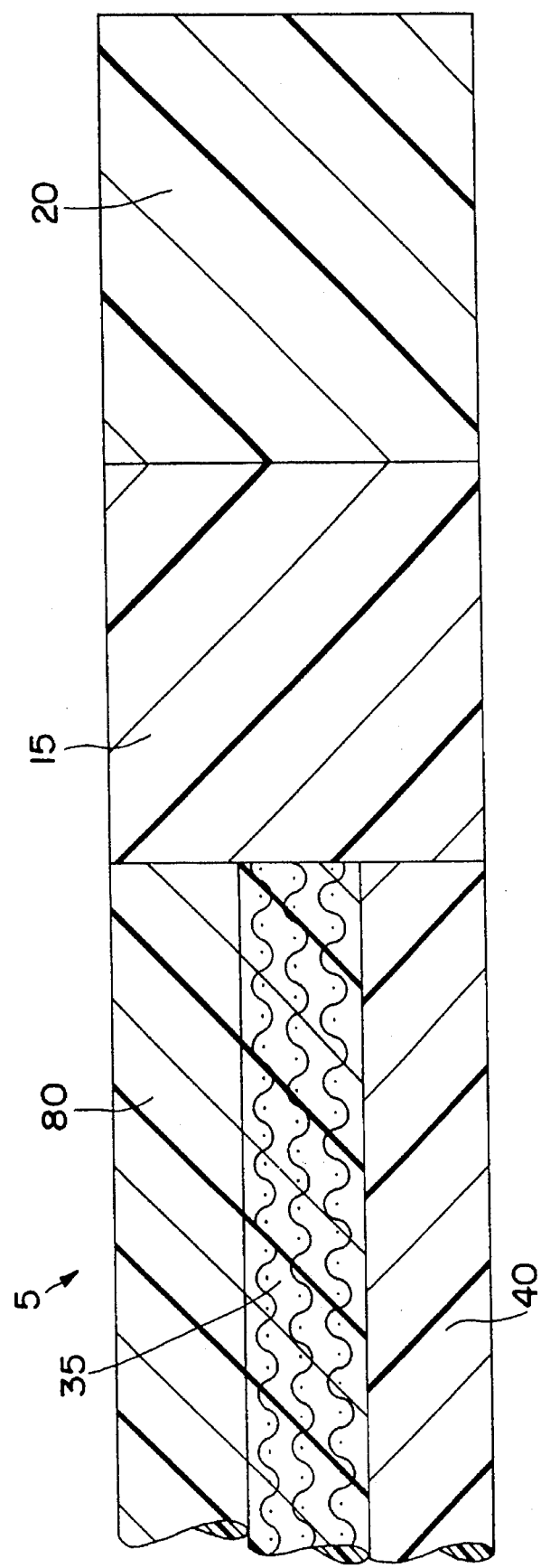
FIG. 7 is a cross-sectional view of the bonded assembly of the catheter shaft, the transition segment and the soft tip segment.

Referring to FIG. 7, a cross-sectional view of the completed assembly of FIG. 4 is shown. The catheter shaft 5 is comprised of principally three layers as shown in FIG. 7: a lubricous TEFLON® liner 40, a composite layer of wire braid 35 and polymer, and an outer jacket polymer 80. The distal end of the catheter shaft 5 is shown bonded to the proximal end of the transition tubing 15 and the distal end of the transition tubing 15 is shown bonded to the proximal end of the soft tip tubing 20.

The selection of materials for the transition tubing 15 is based upon considerations of tensile strength, processing temperature compatibility with the polymers comprising the catheter shaft 5, and flexural modulus. A tensile strength in excess of 45 MPa is necessary to achieve a minimally acceptable bond strength of 18N between the catheter shaft 5 and the transition tubing 15 when the wall thickness of the catheter shaft is less than 0.3 mm. This is because of the compromised bonding between the catheter shaft 5 and the transition tubing 15 caused by the presence of the wire braid in the composite layer 70 and by the TEFLON® in the lubricous liner 40. The 65D transition tubing 15 does not bond to the lubricous liner 40 of TEFLON® because TEFLON® does not adhere well to any materials. The 65D transition tubing 15 does not bond to the wire in the wire braid composite layer 35 which is composed of wire and a polymer. This is a consequence of the primary bonding mechanism which is melt fusing. Since the wire cannot be melt fused to the 65D transition tubing 15, bonding between the 65D transition tubing 15 and the wire braid composite layer 35 is limited to the interstitial sites which are occupied by the 75D polymer of the outer jacket 80. The 65D transition tubing 15 bonds well to the 75D polymer of the outer jacket 80 because of melt compatibility. Because primary bonding occurs only at the interface of the 65D transition tubing 15, and because the 75D polymer of the outer jacket 80 is only approximately one third of the overall catheter wall thickness, the transition tubing 15 must be chosen for its tensile strength.

The cross-sectional area of the bond between the materials of the 65D transition tubing 15 and the polymer of the outer jacket 80 such as 75D Polyurethane is $II/4$ $(0.091^2-0.085^2)=8.3e-4$ $in^2$. The cross-sectional area of the bond between the materials of the 65D transition tubing 15 and the 80A polyurethane soft tip tubing 20 is $II/4$ $(0.091^2-0.072^2)=24.3e-4$ $in^2$. These cross-sectional areas can be related to the force required to break the bond with an axial stress on the bond. Force equals the average tensile strength multiplied by the area. The average tensile strength of 65D is 6800 $lbs/in^2$. The average tensile strength of 80A is 4200 $lbs/in^2$. The force required to break the bond between the 75D polymer of the outer jacket 80 and the 65D transition tubing 15 is 6800 $psi * 8.3e-4$ $in^2=5.6$ lbs. Converted to SI units, the bond strength is 25N. The force required to break the bond between the 65D transition tubing 15 and 80A polyurethane soft tip tubing 20 is 4200 $psi * 24.3e-4$ $in^2=10.2$ lbs. Converted to SI units the bond strength is 45N. Without applicant's transition tubing 15, bonding the 80A polyurethane soft tip tubing 20 directly to the 75D polymer of the outer jacket 80 yields a bond strength of 4200 $lbs/in^2 * 8.33e-4=3.5$ lbs or 15.5N in SI units.

For the transition tubing 15 to bond adequately to the outer jacket polymer 80, the transition tubing 15 must have a processing temperature which is compatible with the outer jacket polymer 80. Further, the transition tubing 15 must exhibit sufficient flexibility to facilitate the manipulation of the catheter shaft 5 through the patient's vasculature. Sufficient flexibility is achieved where the flexural modulus of the transition tubing 15 is less than 250 MPa. To meet the above requirements, the transition tubing 15 is comprised of a Shore 65D PELLETHANE® polyurethane. This material has a compatible processing temperature to the outer jacket polymer 80, which is comprised of Shore 75D PELLETHANE® polyurethane.

The selection of materials for the soft tip tubing 20 is based upon considerations of flexural modulus and tensile strength. The flexural modulus is an indicator of the ability of the polymer to deflect adequately when the soft tip tubing 20 contacts a wall of the patient's vasculature. The tensile strength must be sufficient to ensure an 18N minimum bond strength between the soft tip tubing 20 and the transition tubing 15. For a catheter wall thickness of less than 0.3 ram, a polymer exhibiting a minimum tensile strength of 30 MPa is required for the soft tip tubing 20. These criteria are met with a material such as Shore 80A PELLETHANE® polyurethane.

It is noteworthy that the minimum tensile strength of the material comprising the soft tip tubing 20 is significantly less than that required for the transition tubing 15. This is because of the compromised bonding with the multi-layer catheter shaft 5 which requires a higher tensile strength material to compensate for the poor bonding which occurs between the transition tubing 15 and both the composite layer 70 and the lubricous liner 75. Where the transition tubing 15 is not comprised of multiple layers as is the catheter shaft 5, the soft tip tubing 20 is bonded to the entire wall thickness of the transition tubing 15. Thus, a lower tensile strength is allowable to achieve the minimum bond strength of 18N. To meet the criteria of requisite tensile strength, materials should be chosen for the transition tubing 15 and soft tip tubing 20 with a tensile strength ratio greater than 1.55.

The preceding specific embodiments are illustrative of the practice of the invention. It is to be understood, however, that other expedients known to those skilled in the art or disclosed herein, may be employed without departing from the spirit of the invention or the scope of the appended claims.

| No. | Component |
| --- | --- |
| 5 | Catheter Shaft |
| 10 | Heat Shrink Tubing |
| 15 | 65D Transition Tubing |
| 20 | 80A Soft Tip Tubing |
| 25 | 75D Plug Tubing |
| 30 | Mandrel |
| 35 | Wire Braid Composite Layer |
| 40 | TEFLON ® Liner |
| 45 | Infrared source |
| 50 | Shaft Lumen |
| 55 | Transition Tube Lumen |
| 60 | Tip Tube Lumen |
| 65 | Plug Tube Lumen |
| 80 | Outer Jacket Polymer |

What is claimed is:

1. A catheter comprising:
   (a) an elongated shaft having an inner diameter, a proximal end and a distal end, the shaft defining at least one lumen, the shaft having a lubricous liner coating the inner diameter of the shaft;
   (b) an elongated transition tube having a proximal end and a distal end, the transition tube defining at least one lumen, the proximal end of the transition tubing being affixed to the distal end of the shaft, the transition tube being generally free of the lubricous liner;
   (c) an elongated tip tube having a proximal end and a distal end, the tip tube defining at least one lumen, the proximal end of the tip tube being affixed to the distal end of the transition tube and the tip tube being made of materials having a lower melt temperature than the transition tube, the tip tube being free of the lubricous liner; and
   (d) the elongated transition tube being formed of materials having a tensile strength of at least 150% of the materials comprising the elongated tip tube.

2. A catheter according to claim 1 wherein the shaft consists of 75D durometer tubing.

3. A catheter according to claim 1 wherein the transition tube is approximately 2.5 mm long.

4. A catheter according to claim 1 wherein the transition tube is made of 65D Durometer polyurethane loaded with radiopacifier.

5. A catheter according to claim 1 wherein the transition tube is selected from a group of thermoplastic elastomers having a tensile strength of at least 45 Mpa.

6. A catheter according to claim 1 wherein the tip tube is approximately 0.5 cm long with a tolerance of plus or minus 1 min.

7. A catheter according to claim 1 wherein the tip tube is made of a clear polymer to which titanium dioxide has been added.

8. A catheter according to claim 1 having an elongated plug tube having a proximal end and a distal end, the plug tube defining at least one lumen, the proximal end of the plug tube affixed to the distal end of the tip tube.

9. A catheter according to claim 8 wherein the plug tube consists of approximately 2.5 mm of 75D Durometer tubing.

10. A catheter according to claim 8 wherein a mandrel extends into the distal end of the lumen of the plug tube and exits the proximal end of the lumen of the plug tube, then extends into the distal end of the lumen of the tip tube and exits the proximal end of the lumen of the tip tube, then extends into the distal end of the transition tube and exits the proximal end of the transition tube, and extends into the distal end of the lumen of the shaft.

11. A catheter according to claim 10 wherein the mandrel extends approximately 15.2 cm beyond the distal end of the shaft and is shaped to closely fit within the shaft.

12. A catheter according to claim 10 wherein the mandrel consists of TEFLON® coated stainless steel.

13. A catheter according to claim 1 wherein the distal end of the shaft blends and flows with the proximal end of the transition tube.

14. A catheter according to claim 1 wherein the distal end of the transition tube blends and flows with the proximal end of the tip tube.

15. A catheter according to claim 8 wherein the distal end of the tip tube blends and flows with the proximal end of the plug tube.

16. A catheter according to claim 8 wherein a mandrel extends longitudinally through the shaft lumen, the transition tube lumen, the tip tube lumen and the plug tube lumen and wherein the mandrel, plug tube, tip tube and transition tube are enclosed within a tube of heat shrink material.

17. A catheter according to claim 16 wherein the heat shrink tubing is 10 cm long.

18. A catheter comprising:
  (a) an elongated shaft having an inner diameter a proximal end and a distal end, the shaft defining at least one lumen, the shaft having a reinforcement member embedded at least partially within the shaft and a lubricious liner coating the inner diameter of the shaft;
  (b) an elongated transition tube having a proximal end and a distal end, the transition tube defining at least one lumen, the proximal end of the transition tubing being affixed to the distal end of the shaft, the transition tube being generally free of the lubricious liner;
  (c) an elongated tip tube having a proximal end and a distal end, the tip tube defining at least one lumen, the proximal end of the tip tube being affixed to the distal end of the transition tube and the tip tube being made of materials having a lower melt temperature than the transition tube, the tip tube being free of the lubricious liner; and
  (d) the elongated transition tube being formed of materials having a tensile strength of at least 150% of the materials comprising the elongated tip tube.

19. A catheter according to claim 18 wherein the reinforcement member comprises a wire braid.

20. A catheter comprising:
  (a) an elongated shaft having a proximal end and a distal end, the shaft defining at least one lumen;
  (b) an elongated transition tube having a proximal end and a distal end, the transition tube defining at least one lumen, the proximal end of the transition tubing being affixed to the distal end of the shaft;
  (c) an elongated tip tube having a proximal end and a distal end, the tip tube defining at least one lumen, the proximal end of the up tube being affixed to the distal end of the transition tube and the tip tube being made of materials having a lower melt temperature than the transition tube; and
  (d) the elongated transition tube being formed of 65D Durometer polyurethane that has a tensile strength of at least 150% of that of the elongated tip tube.

21. A catheter comprising:
a transition tube according to claim 20 wherein the transition tube is loaded with a radiopacifier.

22. A catheter comprising:
  (a) an elongated shaft having a proximal end and a distal end, the shaft defining at least one lumen;
  (b) an elongated transition tube having a proximal end and a distal end, the transition tube defining at least one lumen, the proximal end of the transition tubing being affixed to the distal end of the shaft;
  (c) an elongated tip tube having a proximal end and a distal end, the tip tube defining at least one lumen, the proximal end of the tip tube being affixed to the distal end of the transition tube and the tip tube being made of materials having a lower melt temperature than the transition tube;
  (d) the elongated transition tube being formed of materials having a tensile strength of at least 150% of the materials comprising the elongated tip tube; and
  (e) an elongated plug tube having a proximal end and a distal end, the plug tube defining at least one lumen, the proximal end of the plug tube being affixed to the distal end of the tip tube, the plug tube consisting of approximately 2.5 mm of 75D Durometer tubing.

23. A catheter comprising:
  (a) an elongated shaft having a proximal end and a distal end, the shaft defining at least one lumen;
  (b) an elongated transition tube having a proximal end and a distal end, the transition tube defining at least one lumen, the proximal end of the transition tubing being affixed to the distal end of the shaft;
  (c) an elongated tip tube having a proximal end and a distal end, the tip tube defining at least one lumen, the proximal end of the tip tube being affixed to the distal end of the transition tube and the tip tube being made of materials having a lower melt temperature than the transition tube;
  (d) the elongated transition tube being formed of materials having a tensile strength of at least 150% of the materials comprising the elongated tip tube;
  (e) an elongated plug tube having a proximal end and a distal end, the plug tube defining at least one lumen, the proximal end of the plug tube being affixed to the distal end of the tip tube; and
  (f) a mandrel extending longitudinally through the shaft lumen, the transition tube lumen, the tip tube lumen and the plug tube lumen and wherein the mandrel, plug tube, tip tube and transition tube are enclosed within a tube of heat shrink material.

24. A catheter according to claim 23 wherein the heat shrink tubing is 10 cm long.

* * * * *